United States Patent [19]

Maness et al.

[11] Patent Number: 4,856,993
[45] Date of Patent: * Aug. 15, 1989

[54] PRESSURE AND CONTACT SENSOR SYSTEM FOR MEASURING DENTAL OCCLUSION

[75] Inventors: William L. Maness; Robert F. Golden, both of Boston; Michael H. Benjamin, Quincy; Robert M. Podoloff, Cambridge, all of Mass.

[73] Assignee: Tekscan, Inc., Boston, Mass.

[ * ] Notice: The portion of the term of this patent subsequent to Mar. 29, 2005 has been disclaimed.

[21] Appl. No.: 104,731

[22] Filed: Oct. 2, 1987

Related U.S. Application Data

[63] Continuation-in-part of Ser. No. 717,532, Mar. 29, 1985, Pat. No. 4,734,034.

[51] Int. Cl.$^4$ .............................................. A61C 19/04
[52] U.S. Cl. ..................................... 433/68; 73/865.7; 128/777; 338/99; 433/71
[58] Field of Search ............................ 433/68, 69, 71; 128/777, 774, 776, 782; 73/781, 776, 790, 818, 172, 379, 432 T; 340/665, 666; 338/99

[56] References Cited

U.S. PATENT DOCUMENTS

| | | | |
|---|---|---|---|
| 2,951,817 | 9/1960 | Myers | 252/511 |
| 3,349,489 | 10/1967 | Shackelford | 433/68 |
| 3,386,067 | 5/1968 | Costanzo | 338/100 |
| 3,503,031 | 3/1970 | Nybus et al. | 338/99 |
| 3,562,418 | 2/1971 | Glusick et al. | 178/6 |
| 3,974,470 | 8/1976 | DuRocher | 338/99 |
| 4,134,063 | 1/1979 | Nicol et al. | 324/61 R |
| 4,155,262 | 5/1979 | Wong et al. | 338/4 |

(List continued on next page.)

OTHER PUBLICATIONS

"A Forced Transducer Employing Conductive Silicone Rubber," J. P. A. Purbrick, First Robot Vision and Sensors Conference, Stratford-on-Avon, England, Apr., 1981.
Active Touch Sensing, "W. D. Hillis, Artificial Intelligence Laboratory Memo 629," M.I.T., Apr., 1981.
"Pressure Sensitive Material Measures Explosion Forces or Foot Fall of a Fly," *Product Engineering*, Sep. 16, 1957.
"Robotic Tactile Sensing", Kirk E. Pennywitt, Coming to Grips with Tactile Sensors, *Byte*, Jan., 1986, pp. 177–200.
"Reproducibility of Occlusal Marking Techniques", E. Gazit et al., Journal of Prosthetic Dentistry, Apr., 1986, pp. 505–509.

Primary Examiner—John J. Wilson
Attorney, Agent, or Firm—Wolf, Greenfield & Sacks

[57] ABSTRACT

A contact sensor for detecting points on a grid where the sensor is being contacted on opposing sides by teeth surfaces or other contacting points. The sensor is especially useful for measuring dental occlusion. The contact sensor includes two sets of parallel electrodes which are each formed on a thin, flexible supporting sheet. The electrodes are separated by a thin, pressure-sensitive resistive coating such as molydenum disulphide. Two such electrode structures are oriented at approximately right angles to create a grid where the intersecting electrodes cross separated by the resistive coatings. Several arrangements of resistive coating over electrodes as disclosed. In the absence of an external force, the material between the electrodes sets provides a high resistance between intersecting electrodes. The resistance between electrode intersections changes as pressure on opposite sides of the intersection changes. The sensor output is dynamic in that the resistance will vary as external pressure is repeatedly applied and removed. The sensor may be made extremely thin and can provide high resolution capable of distinguishing between contact points separated by 0.050 inches or less.

A new circuit is provided which measures the resistance between each electrode intersection and provides an output representative of the opposing forces at the intersection. The circuit limits the maximum possible current which can flow in the sensor and provides increased resolution in measuring pressure between contacting surfaces.

32 Claims, 5 Drawing Sheets

U.S. PATENT DOCUMENTS

| | | | |
|---|---|---|---|
| 4,163,204 | 7/1979 | Sado et al. | 338/114 |
| 4,208,648 | 6/1980 | Naumann | 338/99 |
| 4,235,141 | 11/1980 | Eventoff | 338/69 |
| 4,268,815 | 6/1981 | Eventoff et al. | 338/69 |
| 4,276,538 | 6/1981 | Eventoff | 338/69 |
| 4,301,337 | 11/1981 | Eventoff | 200/5 A |
| 4,306,480 | 12/1981 | Eventoff | 84/1.01 |
| 4,314,227 | 2/1982 | Eventoff | 338/99 |
| 4,314,228 | 2/1982 | Eventoff | 338/99 |
| 4,315,238 | 2/1982 | Eventoff | 338/99 |
| 4,319,078 | 3/1982 | Yokoo et al. | 338/99 |
| 4,402,326 | 9/1983 | Okano et al. | 433/68 |
| 4,451,714 | 5/1984 | Eventoff | 338/99 |
| 4,488,873 | 12/1984 | Bloomfield et al. | 433/71 |
| 4,492,949 | 1/1985 | Peterson et al. | 338/99 |
| 4,503,416 | 3/1985 | Kim | 338/99 |
| 4,521,186 | 6/1985 | Wodlinger et al. | 128/777 |
| 4,529,959 | 7/1985 | Ito et al. | 338/99 |
| 4,555,953 | 12/1985 | Dario et al. | 73/432 T |
| 4,555,954 | 12/1985 | Kim | 338/99 |

PRESSURE AND CONTACT SENSOR SYSTEM FOR MEASURING DENTAL OCCLUSION

This application is a continuation-in-part of U.S. patent application Ser. No. 717,532, filed Mar. 29, 1985, for A Contact Sensor for Measuring Dental Occlusion, now U.S. Pat. No. 4,734,034, issued 03/29/88.

FIELD OF THE INVENTION

This invention is related to the field of contact sensors, and more particularly to the field of dental occlusal sensors for providing measurements of dental contact points as a patient s jaw is closed.

BACKGROUND OF THE INVENTION

It is frequently desirable or necessary in performing dental diaqnostic procedures to measure the occlusion, or points of contact, between a patient s teeth as the patient closes his or her jaws. Occlusion measurements are necessary, for example in prescribing and fitting many dental appliances such as false teeth or orthodontic devices. Such measurements enable the user to determine where the teeth first contact each other, disclosing high spots and other useful information.

In order to provide an accurate measurement of the occlusion, an occlusal measuring device must be extremely thin so as not to perturb the normal dental alignment. A sensor must also have a very high spatial resolution to provide useful information and distinguish between contact and non-contact points of the teeth. Additionally, a practical sensor must be safe for oral use and should be capable of being used by non-technical personnel with minimal training.

Until recently, the types of occlusal sensors available to dentists for measuring occlusion have been limited. The most common method of measuring dental occlusion is by means of a piece of carbon-paper-like material upon which a patient bites down. Another occlusal sensor uses a thin piece of plastic to provide an imprint of the occlusion which, when illuminated with polarized light, indicates the points of contact by different colors. Other methods exist for performing occlusal analysis, including wax impressions and casts of a patient's teeth, but these methods are expensive, time consuming, and in general are not suitable for large scale use in dental offices.

Recently, a new contact sensor has been developed which detects points where the sensor is being contacted on opposing sides by teeth surfaces. The sensor is extremely thin, on the order of a few thousands of an inch thick, and can provide high spatial resolution capable of distinguishing between contact points separated by 0.050 inches or less. This contact sensor includes two sets of parallel electrodes which are each formed on a thin, flexible supporting sheet. The electrodes are then coated with a thin, pressure sensitive resistive coating. Two such electrode structures are oriented at approximately right angles to create a grid where the intersecting electrodes cross. This sensor is described in co-pending U.S. patent application Ser. No. 717,532 Now U.S. Pat. No. 4,734,034 for A Contact Sensor for Measuring Dental Occlusion, which is incorporated herein by reference.

In this sensor, the pressure-sensitive intermediate layer provides a high resistance between intersecting electrodes when no external pressures are applied to the sensor. The resistance changes abruptly to a comparatively low value at locations where external pressure is applied by two contacting points or surfaces. The sensor resistance will change back and forth between high and low resistance states as external pressure is repeatedly applied and removed, allowing repeated measurements of contacting points to be made by a single sensor. The extreme thinness of the sensor allows occlusion to be measured with little or no alteration of a patient's normal bite, and the high resolution provides detailed information to a dentist or other user about the interaction of dental surfaces. The sensor can simultaneously detect contacts at any electrode intersection. Thus the changing patterns of dental occlusion as a patient bites down on the sensor can be monitored to provide a total representation of the patient's occlusion as the jaw is closed.

SUMMARY OF THE INVENTION

The present invention includes an improvement on the sensor described above and a new circuit which allows a plurality of pressure levels to be detected at the points where opposing surfaces on either side of the sensor make contact through the sensor. The sensor includes two sets of parallel electrodes formed on a thin flexible supporting sheet and which are oriented at approximately right anqles. One set of electrodes is completely coated with a material whose resistance is a function of the pressure applied thereto. The second set of electrodes has the pressure sensitive material deposited over each electrode in stripes alone the electrode with spaces between each stripe. Thus, the second sheet includes a plurality of parallel stripes of pressure sensitive material which are electrically isolated from each other.

The outputs from each set of electrodes are applied to a novel sensing circuit which measures the resistance between each intersection of the opposing electrode sets and which provides an output representative of the force with which two opposing surfaces contact each other. The sensing circuit includes circuitry to limit the maximum possible current which can flow in to the sensor. This ensures that no dangerous currents can flow into or through a patient even under the worst circumstances, such as if a patient bites completely through the sensor and directly contacts the electrodes. The present invention additionally provides increased resolution in measuring the pressure between contacting surfaces while having a higher safety level.

While the present invention is especially suitable for measuring the forces caused by the dental occlusion as person's jaw closes, it should be appreciated that the present invention is applicable to other situations where detecting contacts and measuring forces between two opposing objects is required.

DESCRIPTION OF THE DRAWINGS

The invention may be more fully understood by reading the following description of the preferred embodiment in conjunction with the accompanying drawings, of which:

FIG. 1 shows the overall construction of the sensor of the

DESCRIPTION OF THE PREFERRED EMBODIMENT

Figure 1:
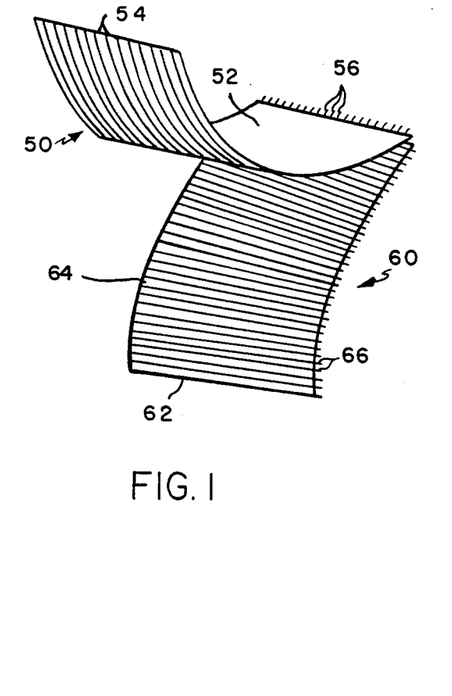

Referring to FIG. 1, the basic structure of the contact sensor used in the present invention is shown. A top layer 50 is fabricated as discussed in detail below. Top layer 50 includes a flexible backing 52 on which are formed parallel rows of electrodes 54. Each electrode is connected to a respective terminal 56 through which electrical contact to the electrode is made. A bottom layer 60 is similarly constructed and includes multiple electrodes 64 formed on a backing 62 and respectively connected to terminals 66.

Figure 2A:
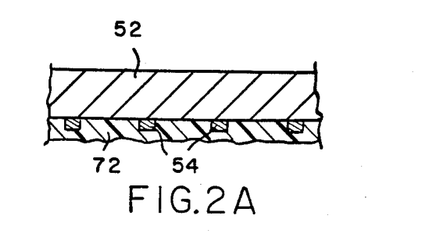
FIGS. 2A & 2B are a magnified view of the relationship of the electrodes and resistive coatinq.
Figure 2B:
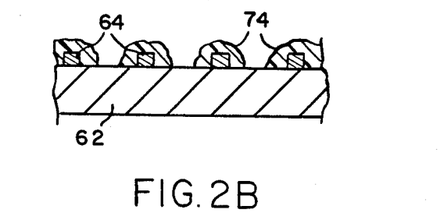

Referring to FIGS. 2A and 2B, the construction of the top and bottom layers of the sensor is shown in more detail. In FIG. 2A, the backing 52 provides a flexible support for row electrodes 54. In the preferred embodiment described herein, backing 52 is formed of a polyester film such as Mylar. Other similar films such as Kapton, manufactured by DuPont, may be used for the backing. These materials combine thinness and strength in a material which can be made into a clean, waterproof package suitable for oral use. Other materials may be used for the backing.

In the preferred embodiment, row electrodes 54 are formed via known methods for making flexible printed circuits. The electrode pattern is applied to the backing 52 by directly printing an electrically conductive ink. Other methods may be used to fabricate the electrodes including photo-etching copper laminated to a mylar or other backing material. Screen printing is best since the resulting conductors are more flexible than solid copper conductors.

Next, the row electrodes are coated with resistive coating 72. Coating 72 is formed of a pressure-sensitive, resistive ink, discussed below, which is applied over the entire surface of the backing sheet 52, as shown in FIG. 2A. Pressure-sensitive resistive inks are materials which can be printed or otherwise applied in thin coatings and which serve to limit the current flowing therethrough.

FIG. 2B shows the construction of the bottom layer 60 which includes column electrodes 64. These electrodes 64 are applied to bottom backing sheet 62 in the same manner as discussed above in connection with the top layer 50 shown in FIG. 2A. Next, the column electrodes 64 are coated with the pressure-sensitive resistive ink. For the column electrodes. however, the ink is applied in stripes 74 which cover each electrode but which do not cover the spaces between the electrode. Thus, each of the stripes 74 of pressure sensitive resistive ink is electrically insulated from adjacent stripes.

To form the entire sensor, the top and bottom layers shown in FIGS. 2A and 2B ar placed together with the electrodes at approximately right angles to each other as shown in FIG. 1, with the resistive coatings 72 and 74 facing one another.

As explained above, the present invention provides improved performance when compared with the sensor described in the above-referenced co-pending application, including the provision of a plurality of output levels representative of different degrees of force between contacting surfaces. In order to optimize the discrimination between different levels, it has been found that a different type of pressure sensitive ink is preferable to the pressure sensitive ink used with the previous embodiment. Typically, the resistive ink used with the embodiment described herein has a cross resistance which is significantly lower than that used with the previous embodiment of the sensor. As a result, the currents flowing between adjacent row or adjacent column electrodes are larger, and may, in fact, affect the accuracy of the sensor. As discussed in more detail below, one of the row and column electrode sets is the "sensed" set. It is only necessary to provide electrical isolation between the pressure sensitive ink over the traces on the sensed side. While the sensed electrodes correspond with the column electrodes in the embodiment described herein, the sensed electrodes could equally well be the row electrodes however.

Figure 3:
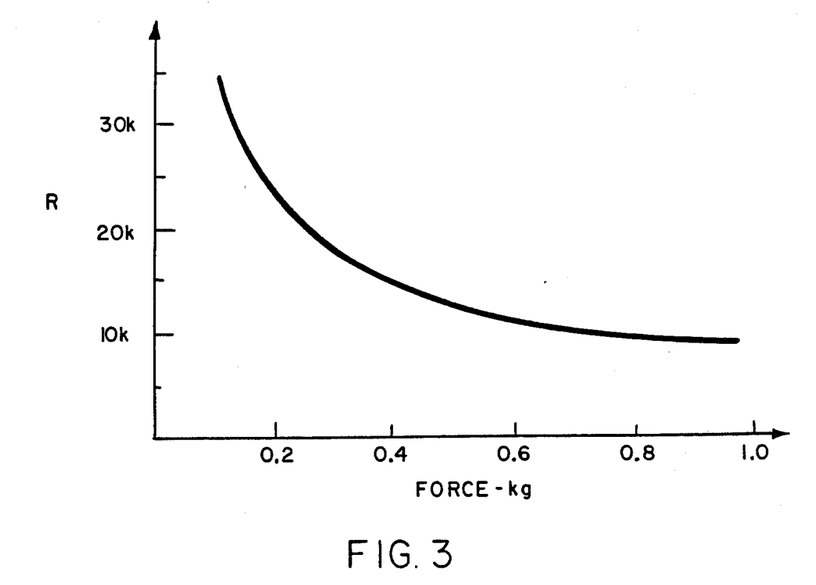
FIG. 3 is a graph showing the relationship of the pressure applied to the resistive material and the resistivity thereof.

In the present invention, the pressure-sensitive, resistive ink has a more linear resistance-to-force characteristic than the material in the sensor described in the above-referenced co-pending application. This enables the sensing circuitry to detect and distinguish between multiple levels of force applied by contacting surfaces. In the preferred embodiment, a resistive ink is used which is composed of a carbon-molybdenum disulfide based ink in an acrylic binder and which has the force versus resistance characteristics shown in FIG. 3. In FIG. 3, the vertical axis represents the measured resistance between row and column electrodes at a particular intersection of the sensor. The horizontal axis represents the force in kilograms applied to the sensor by means of a ⅛ inch diameter steel ball located directly over the intersection whose resistance is being measured.

The technology of formulating and applying resistive inks is well developed. See, for example, *Screen Printing Electronic Circuits,* by Albert Kasoloff, 1980; and National Bureau of Standards Circular No. 530, U.S. Government Printing Office. A resistive ink with the characteristics shown in FIG. 3 may formulated from commercially available components. For example, the following formulation uses products from Acheson Colloids Company in Port Huron, Mich.: 80% dielectric catalog number SS24210, 10% graphite catalog number 423SS, 10% molybdenum disulfide catalog number SS24476. Other inks suitable for use with present invention include Chomerics, Inc., Woburn, Mass., product number 55-01-4402-0000; and Interlink Electronics Company, Santa Barbara, Calif., force sensing resistor formulation.

Figure 4A:
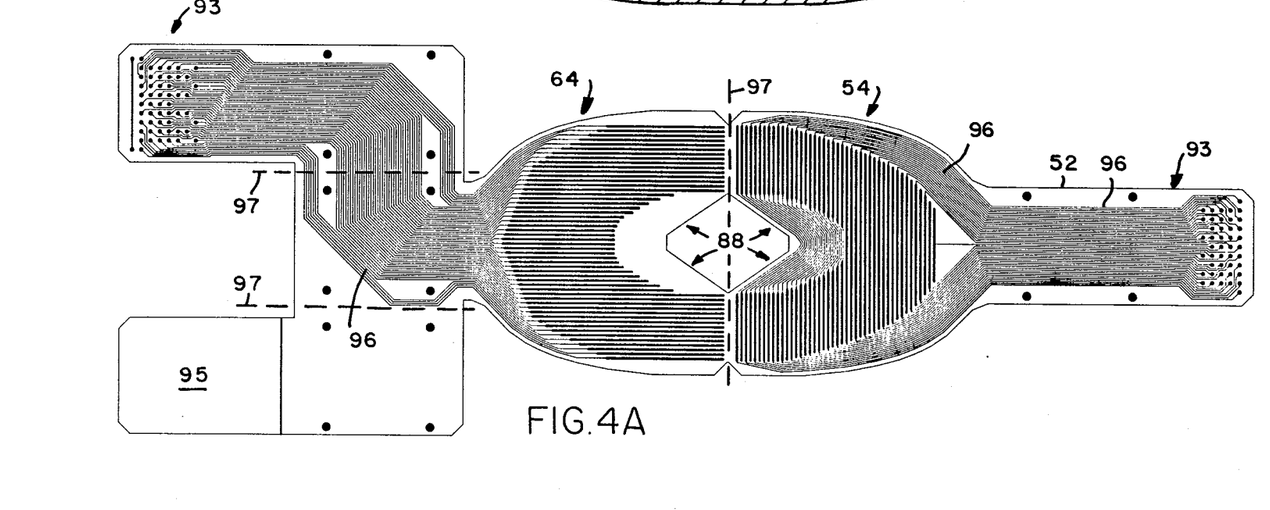
FIGS. 4A and 4B show one configuration for a dental occlusal sensor of the present invention.

A practical sensor for use in dental applications should preferably be disposable to eliminate the need for sterilization between patients. FIG. 4A shows the configuration of a sensor in which the top and bottom electrode arrays are simultaneously formed on a single backing sheet. In FIG. 4A, a backing sheet 52 has column electrodes 64 formed on one half thereof and row electrodes 54 formed on the other half. The row and column electrodes have an area 88 where the teeth make contact with each other from opposite sides of the sensor. Conductive paths 96 are in the area outside the contacting surfaces of the teeth and serve to connect the row and column electrodes 54 and 64 with pads 93 for interconnection with a mating connector.

Figure 4B:
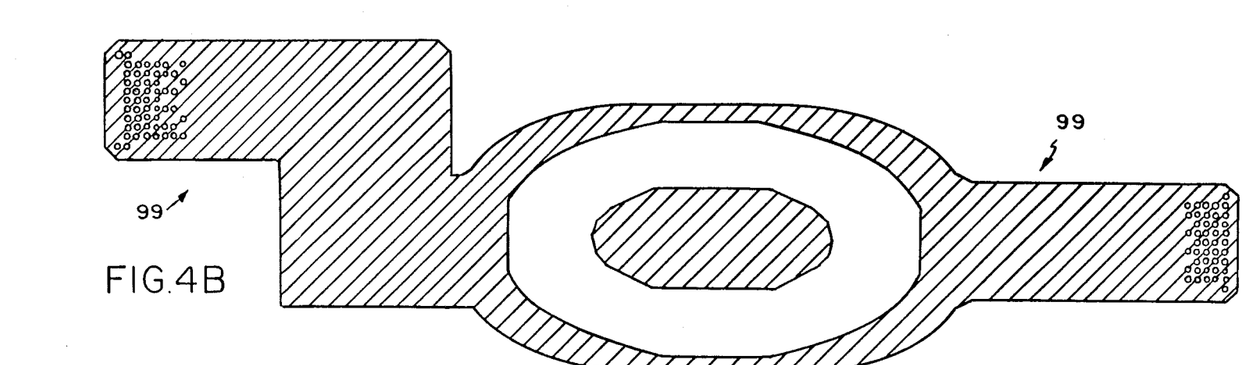

FIG. 4B shows the pattern for an insulating layer which is deposited over the electrode and connector pattern of FIG. 4A. The insulator prevents contacts between the connecting traces 96 when the sensor is folded into its final configuration.

The preferred method for fabricating the sensor begins with printing the conductive traces shown in FIG. 4A on a mylar or other suitable backing sheet through a 325 mesh screen mounted at a 45 degree angle to the row and column traces. Next, the insulating layer shown in FIG. 4B is printed over the conductive trace to cover the entire sensor except for the area where the rows and columns cross. Holes 99 in the insulating layer are provided to allow connection to the sensor via pads 93. The insulating layer is preferably printed through a 200 mesh screen. Next, the pressure-sensitive ink is applied over the row electrodes as a sheet and in stripes over the column electrodes using a 325 mesh screen. In the present embodiment, the column electrodes are 0.030 inches wide and are separated by 0.020 inches. The pressure-sensitive ink deposited over each of these registration tolerance to the columns of ±0.005 inches.

Next, an adhesive material is applied along the edges of the sensor. The sensor is then cut to the shape shown in FIG. 4A from the backing sheet material. By folding the sensor along fold lines denoted by dotted lines 97, the sensor is formed with the row and column electrodes crossing and with the two connecting pad areas 93 adjacent to one another for insertion in a holder, such as holder 92 shown in FIG. 5. Flap 95 folds over the "neck" section containing the conductive traces connecting the rows and columns with the connecting pads 93 to further secure the sensor together.

Figure 5:
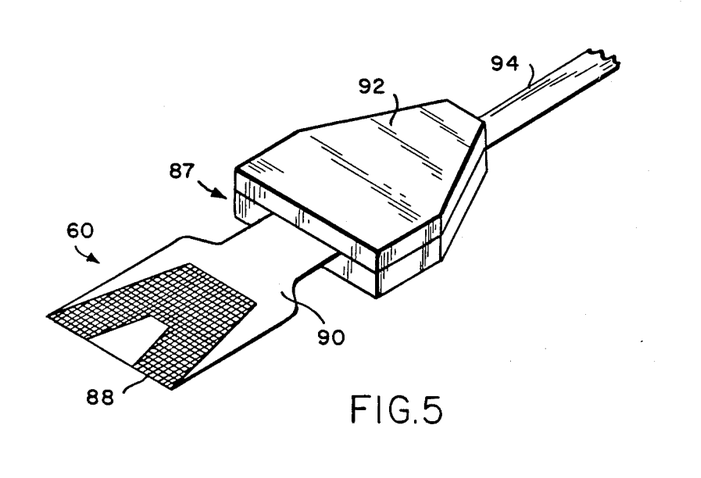
FIG. 5 shows a holder for the sensor.

To make a dental occlusal sensor, the sensor shown in FIG. 4 may be fabricated into a configuration suitable for oral use, such as that shown in FIG. 5. In FIG. 5, the sensor 60 is shown with the electrode area 88 crosshatched to indicate where a patient would bite down on the sensor. The signals from the sensor are applied to the measurement electronics via a multiconductor cable 94 which is attached to the sensor via a connector 92. Signals from the electrodes in area 88 are applied to the connector 92 via conductors within the supporting sheet 90, as described above with reference to FIG. 4A. Connector 92 may make contact directly to the contact pads 93 on the sensor 60 without the necessity for having a matching connector piece attached to the sensor. In this manner, an inexpensive oral sensor may be easily fabricated, allowing for the use of disposable sensors. This greatly increases the ease of use, since sterilization between patients is not required, and also reduces the possibility of transmission of germs due to incomplete sterilization of sensors between uses.

Figure 6:
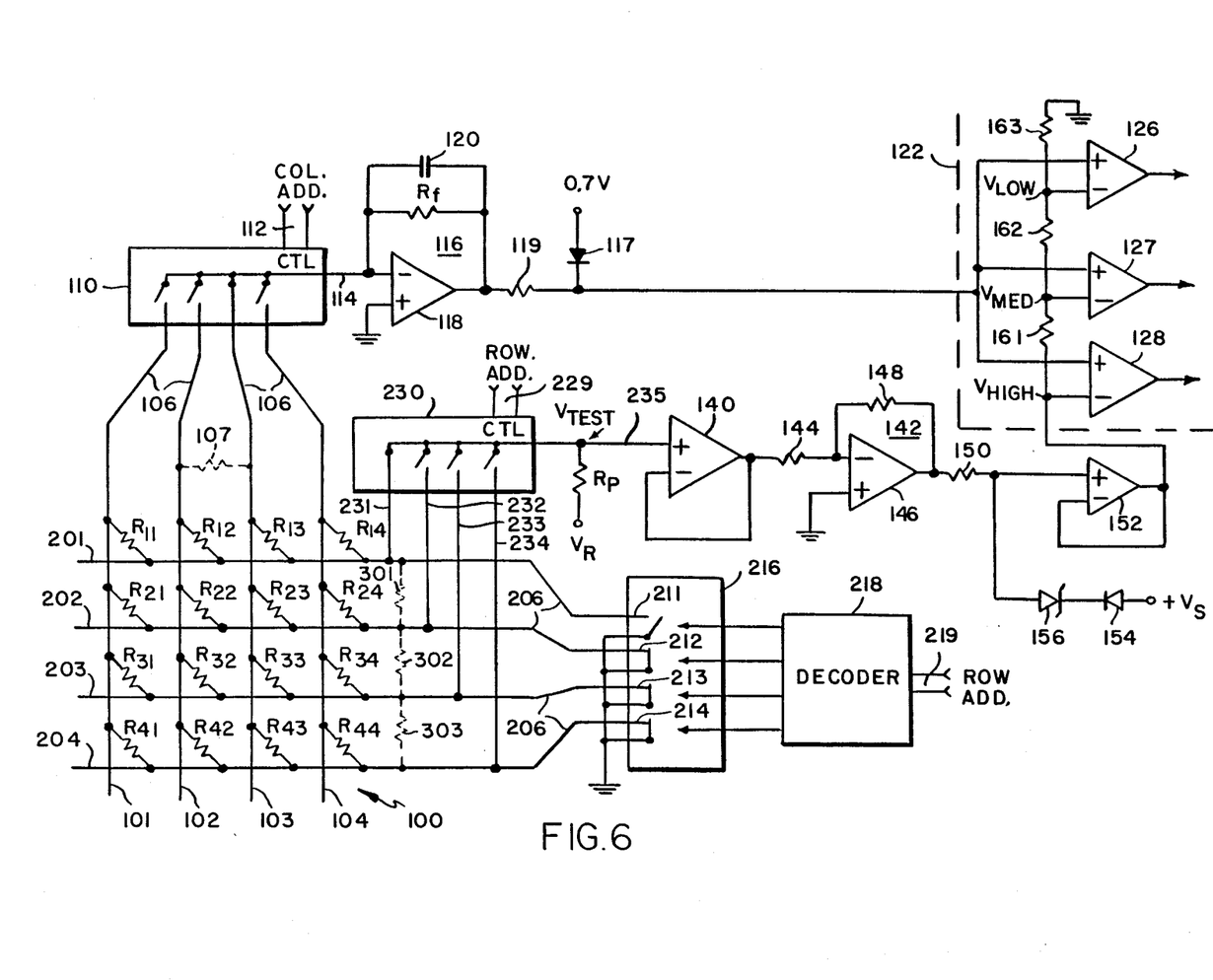
FIG. 6 is a diagram of a simplified circuit which illustrates the advantages of the new sensing circuitry.

Referring to FIG. 6 there is shown an illustrative circuit for reading the output of the sensor described above. As will can measure the resistance at each intersection of the row and column electrodes to provide an indication of the force on opposite sides of the sensor at each of these intersections. The circuit has advantages over previously known circuits, including the sensing circuit described in the above-referenced co-pending application. The circuit shown in FIG. 6 provides greater resolution in measuring pressure, is simpler, and limits the maximum possible current which could be applied to a patient to a level sufficiently low as to be negligible.

In FIG. 6, the sensor is represented by section 100 which shows the intersection of four column electrodes 101 through 104 and four row electrodes 201 through 204. As discussed below, a practical sensor will have many more rows and columns. The intersection of each of the row and column electrodes is characterized by a variable resistance which is a function of the pressure applied to each intersection. These resistances are represented in FIG. 6 by resistors $R_1$ through $R_{44}$, the subscripts indicating the row and column associated with each resistance. The row electrodes 201 through 204 are connected to the circuitry of FIG. 6 through conductors 206 which are part of cable 94.

Each of the row electrodes is connected to an associated single-pole, single-throw analog switch 211–214. Typically, these analog switches are implemented in the form of an integrated circuit 216. The second poles of analog switches 211–214 are connected to ground. Thus, each of the rows 201–204 may be selectively connected to ground by activating the associated analog switch 211–214.

Analog switches 216 are controlled by a digital 2-bit to 4-line decoder circuit 218. In response to a 2-bit row address applied to inputs 219, the decoder activates the corresponding output lines 221–224, opening the corresponding analog switch in circuit 216, while the other three outputs remain low. Thus, circuits 216 and 218 serve to ground all row electrodes except for the electrode designated by the address applied to lines 219.

The row address is also applied to the control inputs of a 4-to-1 analog multiplexer circuit 230. Each of the four multiplexed lines 231–234 of multiplexer 230 is connected to a corresponding row electrode 201–204. A voltage $V_{test}$ is applied to the common input of analog multiplexer 230 and is selectively applied to one of the row electrodes by multipleser circuit 230.

Column electrodes 101–104 are connected by conductors 106 in cable 94 to the inputs of a 4-to-1 analog multiplexer circuit 110. A 2-bit column address signal is applied to the control inputs 112 of multiplexer 110. The common line 114 of multiplexer 110 is connected to the input of an amplifier circuit 116. Thus, in response to the column address signals on lines 112, a selected one of the column electrodes 101–104 is connected to the input of amplifier 116.

Amplifier 116 is a conventional operational amplifier circuit which includes a feedback resistor $R_f$ connecting the inverting input with the output of the op-amp. The non-inverting input of op-amp 118 is grounded. A capacitor 120 is connected in parallel with resistor Rf to insure that high frequency oscillations do not occur. In the preferred embodiment, capacitor 120 has a value of 50 pF, and resistor $R_f$ has a value of 120 kilohms. The output of amplifier 116 is applied to one input of a four level comparator circuit 122.

When the address inputs on lines 112 to multiplexer 110 change, the output from the multiplexer sometimes will contain noise spikes. The noise spikes can saturate the comparator circuitry 122 which follows amplifier 116. The filtering provided by capacitor 120 partially attenuates the spikes. Additionally, a diode 117 is connected between a voltage of 0.7 volts and the output of amplifier 116 taken through a resistor 119. The direction of conduction of diode 117 is from the 0.7 volt source to the amplifier output. Diode 117 ensures that the output from amplifier 116 does not go negative. Such a negative output might saturate the following comparator circuitry.

The $V_{test}$ voltage applied to multiplexer 230 is derived from a reference voltage $V_R$ applied to line 235 via a resistor $R_p$. The reference voltage $V_R$ is a regulated voltage of a fixed value. Current flowing from the regulated voltage supply through resistor $R_p$ provides the $V_{test}$ voltage on line 235. The relative resistances of resistor Rp and the intersection resistances of the sensor 100 determine the value of $V_{test}$, as described in detail below.

By deriving the $V_{test}$ voltage in this manner, the maximum current which can flow into sensor 100 is limited to a value of $V_R/R_P$. This ensures that there is no possibility of a dangerous current flowing through a patient as a result of any malfunction of the sensor. For example, a patient biting completely through the Mylar outside surfaces of the sensor could come directly in contact with one or more of the row electrodes 201-204. The value of resistor $R_p$ limits the maximum current which can flow in the patient in such case and provides an important safety factor. In the preferred embodiment, the value of $V_R$ is $-1.2$ volts and the value of $R_p$ is 18 kilohms resulting in a maximum current of 67 microamps. This value is less than the 70 microamp maximum leakage current for medical devices specified by Underwriters Laboratory Standards.

Comparator circuit 122 includes three two-input comparators 126-128. The output from amplifier 116 is applied to the positive input of each of these comparators. The negative inputs to comparators 126-128 have three different voltages applied thereto. As the output voltage from amplifier 116 goes from zero to a maximum value, the outputs of comparators 126 through 128 will sequentially switch from a low to a high state, providing an output indication of four different voltage levels. These voltage levels represent which of four different force level ranges the measured force lies in.

The reference voltage levels applied to comparators 126 through 128 are derived from the $V_{test}$ voltage present on line 235. As explained further below, the value of the $V_{test}$ voltage will vary depending upon the number of simultaneous contacts detected by sensor 100. As more contacts are made, more current flows from the $V_R$ reference voltage source; and the voltage drop across resistor $R_p$, and hence $V_{test}$, will vary. By taking the reference voltages applied to comparators 126 through 128 from the $V_{test}$ voltage, the outputs from comparator circuit 122 will depend only on the magnitude of the sensor resistance at the intersection currently selected and will be independant of the magnitude of the $V_{test}$ voltage.

The $V_{test}$ voltage is applied to a buffer amplifier comprised of op-amp 140 connected as a voltage follower. The output from buffer amplifier 146 is applied via input resistor 144 to the inverting input of an op-amp 146 in amplifier circuit 142. Feedback resistor 148 connects the output of op-amp 146 with its inverting input. The gain of amplifier circuit 142 is determined by the relative values of resistors 144 and 148. In the preferred embodiment, amplifier stage 142 has a gain of approximately 6.

The output from amplifier 142 is applied via a small value resistor 150 to the input of a buffer amplifier 152. Buffer amplifier 152 is implemented by means of an op amp having its output connected to its inverting input to provide a unity gain amplifier. The output of buffer amplifier 152 is applied to a voltage divider composed of three resistors 161-163 connected in series between the output of the amplifier and ground. The output of amplifier 152 is connected directly to the second input of comparator 128. The junction between resistors 162 and 161 is connected to the inverting input of comparator 127 to provide a reference voltage; and similarly the junction of resistors 162 and 163 provides the reference voltage for comparator 126. Connected between a positive voltage $V_S$ and the non-inverting input of op-amp 152 is a forward biased diode 154 in series with a reverse biased zener diode 156. As described below, these diodes in conjunction with resistor 150 prevent erroneous outputs under certain conditions.

The circuit shown in FIG. 6 operates in the following manner. Each row and column electrode intersection is sequentially scanned to measure the resistance of the pressure-sensitive ink at that intersection to provide an indication of the force applied to the sensor at that intersection. The row and column to be sensed are selected by the column address inputs applied to lines 112 and the row address inputs applied to lines 219. In FIG. 6, the circuitry is shown with row 1 and column 3 selected to measure the resistance of resistor $R_{13}$.

When row 1 is selected, the decoder 218 and analog switches 216 connect rows 2, 3, and 4 to ground. The $V_{test}$ voltage is applied to the row 1 electrode by analog multiplexer circuit 230. Thus $R_{11}$, $R_{12}$, $R_{13}$, and $R_{14}$, all have a non-zero voltage equal to $V_{test}$ applied to their row electrode terminals The selected column line is maintained at virtual ground by op-amp 118, and all row but the selected row are maintained at ground by analog switches 216. Thus, the voltage drop across all resistors connected to the selected column will be zero except for the resistor associated with the selected row. As a result, the current flowing in the connection 106 for the selected column includes only current flowing through the resistor associated with the intersection at the selected row and column. The magnitude of this current, however, depends upon the value of the $V_{test}$ voltage.

The selected column is connected to the input of amplifier 116 by analog multiplexer circuit 110, and the remaining columns are disconnected by the multiplexer. The input to amplifier 116 is kept at virtual ground by the feedback connection of op-amp 118. Thus the current flowing through resistor $R_{13}$ is equal to $V_{test}/R_{13}$. This current is converted into a voltage level and amplified by amplifier 116. The output of amplifier 116 is applied to the input of comparator circuit 122. The individual comparators compare the output from amplifier 116 with the reference voltages applied to their inverting inputs. In this manner, the outputs from comparator circuit 122 provide an indication of which one of the four voltage ranges the output of amplifier 116 falls in.

More than four levels of resolution may be provided by adding additional comparitors to comparitor circuit 122 and additional resistors to voltage divider 161-163. Alternately, comparitor 122 maybe replaced with a ratiometric analog to digital converter. In this case the output of amplifier 152 is applied 116 is applied to the measurement input.

The $V_{test}$ voltage varies as the number of contacts made through the sensor changes. This is due to current which flows through other resistors connecting the unselected columns to the unselected rows which are held at ground. For example, when measuring resistance $R_{13}$ with the circuit connected as shown in FIG. 6, current flows through line 231 through resistor $R_{14}$ and into the fourth column electrode 104. This current then flows through resistors $R_{24}$, $R_{34}$, and $R_{44}$ to the electrodes for rows 1, 2, and 3, which are held at ground by the action of analog switch 216. The values of the resistors in the fourth column will vary depending upon the force applied at each intersection. The same process occurs for unselected columns one and two. Thus, the total current flowing through resistor $R_p$ depends upon the number, location, and intensity of contacts made. By deriving the reference voltages applied to comparators 126–128 from the $V_{test}$ voltage, the output from comparator circuit 122 is independant of the number of contacts made through the sensor. As a result, the output from the comparator 122 is a function of only the resistance at the selected row and column intersection.

This can be seen from the following explanation. Assume again that the resistance $R_{13}$ is being measured. For a given set of contacts and pressures, a current of value $I_1$ will flow through resistor $R_p$ to generate the $V_{test}$ voltage. Part of this current will flow through the resistor at the selected intersection, and part of the current will flow through other resistors. Next assume that the contacts at locations other than the selected intersection change so that the total current flowing through resistor $R_p$ changes. This will result in a test voltage of $K * I_1 * R_p$, where K represents the factor by by a factor of K, and the current flowing through resistor $R_{13}$ will also change by a factor of K. This causes the output voltage from amplifier 116 to similarly change by a factor of K. The reference voltages applied to comparators 126–128 are also derived from $V_{test}$, and each of these reference voltages will similarly change by a factor of K. Since both voltages applied to the two inputs of comparators 126–128 change by the same proportional amount, the comparator output, indicating which of the two voltages is larger, is independant of the value of $V_{test}$.

Figure 7:
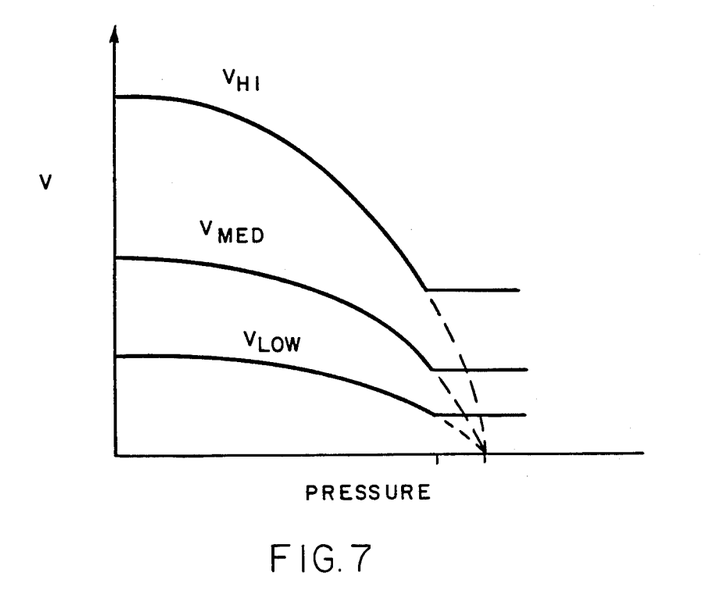
FIG. 7 is a graph which illustrates the variance in threshold levels of the sensing circuitry as the total current through the sensor varies.

FIG. 7 illustrates the variance in the threshold voltages in comparitor 122 as the total current through the sensor changes. In FIG. 7, the horizontal axis represents the pressure at a particular electrode intersection. The vertical axis represents voltage. Three lines are shown on FIG. 7 representing the high, medium, and low threshold voltages applied to comparators 126–128. At low pressures, small amounts of current flow through the resistance at the selected intersection, the $V_{test}$ voltage is relatively high, and the threshold voltages are as shown on the left hand side of the graph. As the pressure increases, the resistance at the selected intersection decreases. This causes additional current to flow through resistor $R_p$ and reduces the value of the $V_{test}$ voltage. Since the reference voltages applied to the comparators 126–128 track the $V_{test}$ voltage, the threshold voltages for the three comparators similarly decrease. Due to the non-linear resistance versus force characteristics of the ink, the pressure versus voltage curve of FIG. 7 is also non-linear.

Diodes 154 and 156 connected between a positive voltage $V_s$ and the input to amplifier 152 ensure that the reference voltages applied to comparators 126–128 do not fall below a selected value. As more contacts are made through the contact sensor, the $V_{test}$ voltage will decrease. As the $V_{test}$ voltage decreases, the voltages applied to the comparators will also decrease. At some point, the difference between these voltages is sufficiently low that noise in the circuit, such as AC interference picked up by cable 94, may cause erroneous results. Diode 154 and zener diode 156 ensure that the voltage applied to the voltage divider which provides the comparator reference voltages does not go below a selected minimum value. Resistor 150 limits the current output from op-amp 146 as a protective measure.

In the absence of the threshold limiting provided by diodes 154 and 156, the three thresholds would intersect the horizontal axis at a point where the resistance across the intersection is equal to zero, as shown by the dashed lines in FIG. 7. At this point, the $V_{test}$ voltage would also be zero. As this condition is approached, the circuit will become more and more susceptible to noise. The threshold limiting circuit avoids this by causing the threshold voltages to remain constant for further increases in pressure once the threshold voltage is reached.

Although the above explanation is in terms of a single intersection resistance, the same process occurs as multiple contacts are made through the sensor. The total current through the $R_p$ resistor is a function of all currents flowing through the sensor, and thus as more contacts are made over the entire area of the sensor, $V_{test}$ and the threshold voltages for comparators 126–128 decrease.

The threshold circuit also provides protection against a short between a row and column electrode. If such a short occurred without the threshold circuit, the sensor and circuitry would produce unreliable or random results along each intersection associated with the shorted column since both input voltages to each comparator would be zero. The threshold circuit described prevents this from occurring. In the presence of a short, the threshold circuit will result in no outputs being present for the shorted row. This is preferable in displaying the data to a diagnostician, since adjacent, non-shorted rows are likely to provide indications of contact points in the vicinity of the shorted row.

The leakage current through zener diode 156 before it reaches its zener breakdown potential may be significant. Leakage current through zener diode 156 will flow through resistor 150 and produce a higher threshold than is desired. Thus, it is important to maintain resistor 150 at a low enough value to ensure that any leakage current through the zener diode does not appreciably affect the threshold voltages applied to comparator circuit 122. In the present embodiment, resistor 150 has a value of 47 ohms.

Prior art circuits similar to FIG. 6 have used a fixed reference voltage in place of $V_{test}$ to drive the row electrodes, however, such a solution does not provide the current limiting performance necessary to insure that a patient is not put in danger. In the present invention, $V_{test}$ decreases as the number of contacts increases to limit the maximum current.

As the number of contacts increases, the current through resistor $R_p$ increases and the value of $V_{test}$ decreases. This effectively lowers the reference current driven through the resistance at the selected intersection. As a result, the resolution between the pressure levels which can be obtained is potentially decreased. In actual practice, however, this is not a problem because in a typical occlusion there are relatively few contacts and it is the first few contacts which are most important. It is for these first few contacts that high resolution is necessary to accurately measure the contacts and pressures. Thus, the circuit shown in FIG. 6 effectively lowers the reference current level as multiple contacts are made to ensure the safety of the patient.

As discussed above, the preferred embodiment of the present invention requires that on set of electrodes have the resistive ink deposited thereupon in stripes which are insulated from one another. The reason for this can be seen by referring to FIG. 6. In FIG. 6, the row electrodes are the driven electrodes and are completely covered by a layer of pressure-sensitive resistive ink 72 covering all electrodes, as shown in FIG. 2A. As a result, currents may flow through the resistive ink between row electrodes. The inter-row resistances are represented in FIG. 6 by resistors 301-303. Current flowing through these resistors will not affect the measurement, since none of these currents will flow through the resistance being measured at the selected intersection.

The column electrodes are the sensed electrodes, and it is important that they be electrically isolated from one another, and thus the pressure-sensitive resistive ink is deposited in stripes over each column electrode to maintain electrical isolation between the electrodes. If the pressure-sensitive resistive ink were deposited across the entire column electrode set, current could flow through the inter-column electrode resistances into the selected column electrode. This is illustrated by resistor 107 shown connected between column two and column three. This resistance represents the inter-column electrode current path which would be present if the pressure-sensitive resistive ink connected the column two and column three electrodes. Current would then flow from row electrode 201 through resistor $R_{12}$, through column electrode 102, and finally through resistor 107 into column electrode 103. This leakage current would affect the output voltage from op amp 118 and would result in an erroneous measurement of the resistance $R_{13}$.

It is preferable to deposit pressure resistive ink on both protection against voids in the pressure resistive ink which occur during the printing process. Dust particles and other contamination may cause small holes in the pressure resistive ink. If only the row electrodes were coated, for example, a single hole over a row electrode could result in a short between that electrode and the opposed column electrode. By coating both the column and row electrodes with pressure resistive ink, shorts will not occur unless imperfection in the deposited ink layers are opposite one another.

Other arrangements for the pressure resistive ink will also work. For example, the row electrodes could be coated with stripes, similarly to the column electrodes. The disadvantage to this arrangement is that depositing stripes on the row electrodes requires a more precise printing process and thus complicates the fabrication of the sensor. Thus, in the preferred embodiment, the row electrodes are covered with a solid layer of resistive ink while the column electrodes are coated with stripes. An operational sensor can be fabricated with any of the following combinations of resistive coatings for rows and columns respectively: solid and stripes; solid and no-coating; stripes and stripes; stripes and no coating; and no-coating and stripes With the circuit shown in FIG. 6, the resistances at several intersections along a single row may be measured simultaneously. In other words, multiple column measurements may be made at the same time to determine the resistance between each measured column and the selected row. To measure the impedances at multiple columns, individual measuring circuitry must be provided for each column being measured, including amplifier 116 and comparator circuit 122. The voltage divider 161-163 providing the three threshold voltages may be shared between the column measurement circuits.

Figure 8:
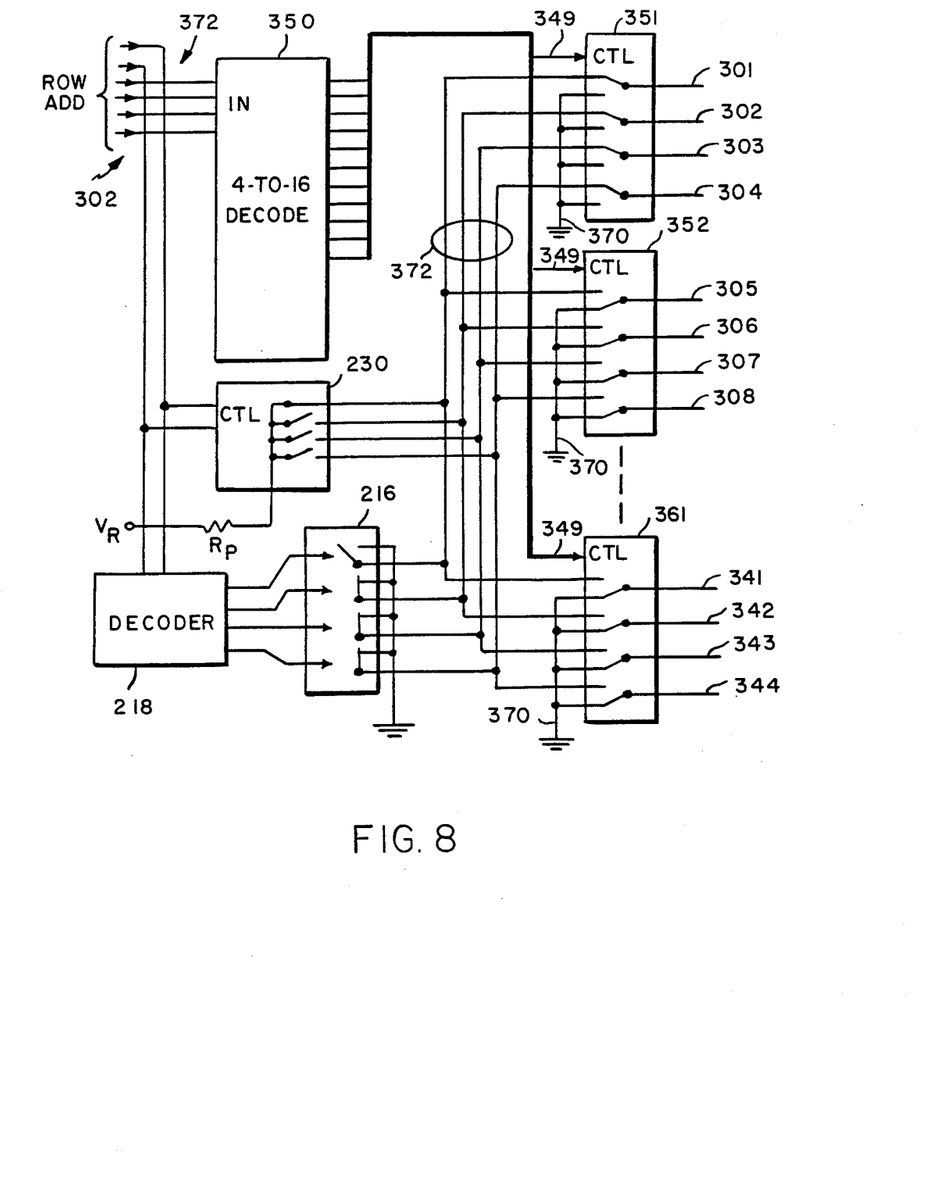
FIG. 8 shows how a circuit such as that of FIG. 6 may be adapted to drive a larger number of row electrodes.

In the preferred embodiment, four columns are measured simultaneously. Each column produces two bits of output data representative of four possible levels, and the outputs from the four measured columns may be read by a computer as a single 8-bit byte. As described below, the preferred sensor includes 52 rows by 44 columns. It is desirable to perform each scan of all the points in the sensor within a time period of about ten milliseconds or less. Using four individual circuits to concurrently measure the resistances at four points, the measurement interval for each point is approximately 17 microseconds. The circuitry shown in FIG. 6 is fast enough so that the comparator outputs settle to their final values within this 17 microsecond time period. FIG. 8 shows an alternate embodiment for implementing the circuitry driving the row electrodes. In FIG. 8, a 6-bit row address, which might be provided from a row counter for example, is applied to lines 302. The two least significant bits are applied to a 2-bit to 4-line decoder 218. The four outputs of decoder 218 are applied to a guard analog switch 216. Decoder 218 and switches 216 operate in essentially the same manner as described above in connection with FIG. 6 The two least significant bits of the row address are also applied to a 4-to-1 analog multiplexer 230. In response to the row addresses applied to multiplexer 230. it sequentially connects lines in bus 372 to the $V_{test}$ voltage, as described above in connection with FIG. 6.

The four most significant bits of the row address are applied to a 4-bit to 16-line decoder 350. The 44 column electrodes are divided into eleven sets of four, as described below, and eleven outputs from decoder 350 are used to select between these eleven different sets.

Connections to each of the 44 row electrodes are made to eleven guad 2-to-1 analog multiplexers 351-361. The first four row electrodes 301-304 are applied to multiplexer 351, the second four electrodes 305-308 are applied to multiplexer 352, and so forth through the last four electrodes 341-344 which are applied to multiplexer 361.

Each of the row electrodes is selectively connected to one of two outputs by the guad multiplexers 351-361 in response to control signals applied to the multiplexer control inputs 349. When the control signal is low, the row electrodes are connected to the ground connections designated as 370 in FIG. 8.

The second four outputs from each of the multiplexers are connected to a four line bus 372. The eleven outputs from decoder 350 are applied to the control inputs 349 of multiplexers 351-361, each of the decoder outputs controlling the state of the switches in the associated multiplexers. Thus, as the four most significant bits of the row address are incremented, analog multiplexers 351-361 are sequentially enabled to connect the associated row electrodes to the lines on bus 372. The row electrodes associated with non-selected multiplexers are grounded via connections 370. The four lines of bus 372 are connected to the four outputs from analog switches 216 and multiplexer 230.

The circuit shown in FIG. 8 operates in the following manner. Assume that the row address outputs applied to line 302 are low. Decoder 350 will enable multiplexer 351, connecting the first four row electrodes to the lines of bus 372. With the two least significant bits equal to 00, multiplexer 230 and analog switches 216 connect the first line of bus 372 to the $V_{test}$ voltage and ground the remaining three lines. Thus the first row electrode 301 is connected to the V$_{test}$ voltage and the remaining electrodes 302-344 are connected to ground. As the two least significant bits of the row address cycle through their four possible states, multiplexer 230 and switches 216 sequentially connect each of the lines in bus 372, and thus the first four row electrodes, to the V$_{test}$ voltage while grounding the remaining lines. After the first four lines have been measured, the third least significant bit of the row address 302 is incremented. This disables analog multiplexer 351 and enables multiplexer 352, connecting the second four row electrodes to bus 372. The above described process is then repeated to measure the intersection resistances for the second four rows. In this manner, a set of 44 row electrodes may be efficiently driven by the circuitry shown in FIG. 8.

It should be appreciated that the present invention as described herein may be modified or adapted in applying the principles of the invention to different situations. Accordingly, the embodiments described herein should not be taken as a limitation on the scope of the present invention, but rather the invention should only be interpreted in accordance with the following claims.

What is claimed is:

1. Apparatus for measuring a person's dental occulsion, comprising:
    a thin, flexible sensor, including:
        a plurality of flexible parallel electrodes attached to and supported by a thin flexible backing sheet to provide a set of driven electrodes;
        a second plurality of flexible, generally parallel electrodes attached to and supported by a thin flexible backing sheet to provide a set of sensed electrodes;
        a resistive layer applied to at least one of the sensed and driven electrode sets and made of a resistive material whose resistance changes as a function of the pressure applied thereto;
        means for positioning the driven and sensed electrodes so that the two electrodes sets face one another separated by the resistive layer so as to form a thin, flexible sensor with the electrodes oriented at an angle to one another so that the electrodes of one set cross the electrodes of the other set at an angle to create a plurality of intersections where driven electrodes cross over sensed electrodes;
        the resistive layer having a thickness substantially less than the spacing between the electrodes and being arranged so as to provide a layer of resistive material between the driven and sensed electrodes at each intersection while maintaining comparative electrical isolation between the individual sensed electrodes in the absence of pressure applied to the sensor;
        said means for positioning being such as to allow insertion of the sensor into the person's mouth so that the facing electrode sets are between the person's upper and lower teeth; and
    measuring means connected to the sensed and driven electrodes for measuring the resistance between the driven and sensed electrodes at each intersection and for providing an output in response thereto representative of the force between contacting points of the person's bite.

2. The apparatus of claim 1 wherein the measuring means includes limiting means for preventing the total current flowing through the sensor from exceeding a predetermined limit.

3. The apparatus of claim 2 wherein the limiting means further includes:
    means for providing a test voltage at a test voltage terminal and for preventing current flowing through the test voltage terminal from exceeding a predetermined level; and
    means for sequentially connecting the test voltage terminal to each of the driven electrodes to apply the test voltage thereto.

4. The apparatus of claim 3 further including means, operative during the time that the test voltage is applied to a driven electrode, for grounding the other driven electrodes to which the test voltage is not applied.

5. The apparatus of claim 4 further including means, operative during the time that each driven electrode has the test voltage applied thereto, for sequentially selecting one or more sensed electrodes and for maintaining the selected one or more sensed electrodes at substantially ground potential while measuring the current flowing through each selected sensed electrode, whereby the ratios of the measured currents to the test voltage provides a representation of the force between contacting points on opposite sides of the sensor at the electrode intersections.

6. The apparatus of claim 5 wherein the means for providing a test voltage includes a reference voltage source and a resistor connecting the reference voltage to the test voltage terminal.

7. The apparatus of claim 6 wherein the values of the reference voltage and the resistor are chosen so as to limit the current flowing through the sensor to a value less than approximately 70 microamps.

8. The apparatus of claim 2 wherein the predetermined current limit is approximately 70 microamps.

9. The apparatus of claim 2 wherein the measuring means further includes:
    means for sequentially applying a test voltage to each of the driven electrodes;
    means responsive to the test voltage for providing an intermediate signal representative thereof such that the intermediate signal is proportional to the test voltage when the test voltage is above a predetermined threshold and so that the predetermined signal is maintained at a fixed value for test voltages below said threshold; and
    means for comparing the current flowing through a selected sensed electrode with the intermediate signal to provide a representation of the resistance between the selected sensed electrode and the driven electrode to which the test voltage is applied.

10. The apparatus of claim 2 wherein the measuring means further includes means responsive to a direct contact between a sensed electrode and a driven electrode for causing the measuring means to provide a predetermined output as representative of the force between intersections along the corresponding sensed electrode.

11. The apparatus of claim 2 wherein the resistive material includes graphite and molybdenum disulfide.

12. The apparatus of claim 2 wherein the first and second plurality of generally parallel electrodes are formed on a single backing sheet and arranged so that they face one another and cross one another at an angle when the backing sheet is folded.

13. The apparatus of claim 12 wherein the backing sheet is formed of a polyester material.

14. The apparatus of claim 1 wherein the resistive material includes graphite and molybdenum disulfide.

15. The apparatus of claim 1 wherein the first and second plurality of generally parallel electrodes are formed on a single backing sheet and arranged so that they face one another and cross one another at an angle when the backing sheet is folded 16. The apparatus of claim 1 wherein the backing sheet supporting the sensed electrodes includes an isolation area between each pair of adjacent sensed electrodes to which the resistive material is not applied.

17. The apparatus of claim 16 wherein the resistive layer includes a stripe of said resistive material applied to each of the sensed electrodes, each stripe of resistive material being physically separated from strips of resistive material over adjacent sensed electrodes.

18. The apparatus of claim 17 wherein the resistive layer further includes a layer of resistive material applied to the driven electrodes.

19. The apparatus of claim 18 wherein the resistive layer applied to the driven electrodes is a continuous layer over the driven electrodes.

20. The apparatus of claim 18 wherein the resistive layer applied to the driven electrodes includes a strip of said resistive material over each driven electrode.

21. The apparatus of claim 16 wherein the resistive layer includes a continuous layer of resistive material applied to the driven electrodes and wherein the sensed electrodes do not have a layer of resistive material applied thereto.

22. A sensor for measuring opposing forces at a plurality of locations comprising:
   a plurality of flexible, generally parallel electrodes attached to and supported by a thin flexible backing sheet to provide a set of driven electrodes;
   a second plurality of flexible, generally parallel electrodes attached to and supported by a thin flexible backing sheet to provide a set of sensed electrodes;
   a resistive layer applied to at least one of the sensed and darien electrode sets and made of a resistive material whose resistance changes a function of the pressure applied thereto;
   the backing sheet supporting the sensed electrodes including an isolation are between each pair of adjacent sensed electrodes to which the resistive material is not applied;
   means for positioning the driven and sensed electrodes so that the two electrodes sets face one another separated by the resistive layer so as to form a thin, flexible sensor with the electrodes oriented at an angle to one another so that the electrodes of one set cross the electrodes of the other set at an angle to create a plurality of intersections where driven electrodes cross over sensed electrodes;
   the resistive layer having a thickness substantially less than the spacing between the electrodes and being arranged so as to provide a layer of resistive material between the driven and sensed electrodes at each intersection while maintaining comparative electrical isolation between the individual sensed electrodes in the absence of pressure applied to the sensor.

23. The apparatus of claim 22 wherein the resistive layer includes a stripe of said resistive material applied to each of the sensed electrodes, each strip of resistive material being physically separated from stripes of resistive material over adjacent sensed electrodes.

24. The apparatus of claim 23 wherein the resistive layer further includes a layer of resistive material applied to the driven electrodes.

25. The apparatus of claim 24 wherein the resistive layer applied to the driven electrodes is a continuous layer over the driven electrodes.

26. The apparatus of claim 24 wherein the resistive layer applied to the driven electrodes includes a stripe of said resistive material over each driven electrode.

27. The apparatus of claim 22 wherein the resistive layer includes a continuous layer of resistive material applied to the driven electrodes and wherein the sensed electrodes do not have a layer of resistive material applied thereto.

28. The apparatus of claim 22 further including measuring means connected to the sensed and driven electrodes for measuring the resistance between the driven and sensed electrodes at each intersection and for providing an output in response thereto representative of opposing forces on opposite sides of the sensor, the measuring means including limiting means for preventing the total current flowing through the sensor from exceeding a predetermined limit.

29. The apparatus of claim 28 wherein the limiting means further includes:
   means for providing a test voltage at a test voltage terminal and for preventing current flowing through the test voltage terminal from exceeding a predetermined level; and
   means for sequentially connecting the test voltage terminal to each of the driven electrodes to apply the test voltage thereto.

30. The apparatus of claim 29 further including means, operative during the time that the test voltage is applied to a driven electrode, for grounding the other driven electrodes to which the test voltage is not applied.

31. The apparatus of claim 30 further including means, operative during the time that each driven electrode has the test voltage applied thereto, for sequentially selecting one or more sensed electrodes and for maintaining the selected one or more sensed electrodes at substantially ground potential while measuring the current flowing through each selected sensed electrode, whereby the ratios of the measured currents to the test voltage provides a representation of the force between contacting points on opposite sides of the sensor at the electrode intersections.

32. The apparatus of claim 31 were in the means for providing a test voltage includes a reference voltage source and a resistor connecting the reference voltage to the test voltage terminal.

* * * * *